United States Patent [19]

Umezawa et al.

[11] 4,167,448

[45] Sep. 11, 1979

[54] PROCESS FOR PREPARATION OF PHYSIOLOGICALLY ACTIVE PEPTIDES

[75] Inventors: Hamao Umezawa, Tokyo; Takaaki Aoyagi, Fujisawa; Tomio Takeuchi, Tokyo; Masa Hamada, Hoya, all of Japan

[73] Assignee: Zaidan Hojin Biseibutsu Kagaku Kenkyu Kai, Tokyo, Japan

[21] Appl. No.: 916,184

[22] Filed: Jun. 16, 1978

Related U.S. Application Data

[62] Division of Ser. No. 834,635, Sep. 19, 1977, Pat. No. 4,126,606.

[30] Foreign Application Priority Data

Oct. 4, 1976 [JP] Japan .................................. 51/119089
Jul. 22, 1977 [JP] Japan .................................. 52/88729

[51] Int. Cl.² ...................... A61K 35/74; C12D 13/06
[52] U.S. Cl. ......................................... 435/70; 435/886
[58] Field of Search ....................................... 195/80 R

[56] References Cited

U.S. PATENT DOCUMENTS

| 3,869,347 | 3/1975 | Umezawa et al. | 260/112.5 R |
| 3,878,185 | 4/1975 | Murao et al. | 260/112.5 R |
| 4,029,547 | 6/1977 | Umezawa et al. | 195/80 R |
| 4,070,458 | 1/1978 | Umezawa et al. | 424/177 |

OTHER PUBLICATIONS

Aoyagi et al., Journal of Antibiotics, vol. 31, No. 6, pp. 636–638, (Jun. 1978).
Journal of Antibiotics, vol. 29, pp. 97–103, (Jan. 1976), pp. 600–601, (May 1976).

*Primary Examiner*—Lionel M. Shapiro
*Attorney, Agent, or Firm*—Herbert W. Taylor, Jr.

[57] ABSTRACT

The present invention relates to new physiologically active peptides, derivatives thereof and a process for preparation thereof. In particular, it relates to new tetrapeptides designated amastatins $A_1$, $A_2$, $A_3$, $B_1$ and $B_2$ and derivatives thereof which have an inhibitory effect on aminopeptidase A and also show stimulation of antibody formation and to a process for preparation thereof by cultivating a strain belonging to the genus Streptomyces.

2 Claims, No Drawings

PROCESS FOR PREPARATION OF PHYSIOLOGICALLY ACTIVE PEPTIDES

CROSS REFERENCE TO RELATED APPLICATION

This application is a division of our prior, copending application Ser. No. 834,635 filed Sept. 19, 1977, now U.S. Pat. No. 4,126,606, issued Nov. 21, 1978.

FIELD OF THE INVENTION

The present invention relates to new physiologically active peptides, derivatives thereof and a process for preparation thereof. In particular, it relates to new tetrapeptides designated amastatins $A_1$, $A_2$, $A_3$, $B_1$ and $B_2$ and derivatives thereof which have an inhibitory effect on aminopeptidase A and also show stimulation of antibody formation and to a process for preparation thereof by cultivating a strain belonging to the genus Streptomyces.

DESCRIPTION OF THE PRIOR ART

Several physiologically active peptides or N-acylated peptides have been found in the culture broths by some of the present inventors. These substances, e.g. leupeptin, antipain, chymostatin and pepstatin, inhibit trypsin, papain, chymotrypsin and pepsin, respectively, but all these inhibitors have their effects on proteases which act in endo-type reaction. For further disclosures of these see Enzyme Inhibitors of Microbial Origin, Hamao Umezawa, University of Tokyo Press (1972) in Chapter IV, Inhibitors of Proteolytic Enzymes (pages 15–52) as follows:

| Peptides | Page Number |
| --- | --- |
| Leupeptin | 15 |
| Antipain | 29 |
| Chymostatin | 32 |
| Pepstatin | 34 |

Bestatin, which has also been found in a microbial culture broth, inhibits an exo-type proteolytic enzyme, i.e. aminopeptidase B and leucine aminopeptidase, but it does not have any inhibitory effect on aminopeptidase A [J.Antibiotics 29, 97–103 and 600–601 and U.S. Pat. No. 4,029,547].

SUMMARY OF THE INVENTION

There are provided by the present invention the physiologically active peptides amastatins $A_1$, $A_2$, $A_3$, $B_1$ and $B_2$ of the formula I $$X—Val—Val—Y \qquad I$$

wherein,

X represents 3-amino-2-hydroxy-5-methylhexanoyl or 3-amino-2-hydroxy-4-methylhexanoyl residue, Val represents L-valyl residue, and Y represents L-aspartic acid, L-glutamic acid or L-aspartic acid α-amide when X is 3-amino-2-hydroxy-5-methylhexanoyl residue, and L-glutamic acid or L-glutamic acid α-amide when X is 3-amino-2-hydroxy-4-methylhexanoyl residue, and the amino group of Val adjacent to X being acylated with the carboxyl group of X to form an amide bond, the carboxyl group of said Val acylating the amino group of the other Val to form an amide bond, and the carboxyl group of the other Val acylating the amino group of Y to form an amide bond.

There is further provided by the present invention a process for producing amastatins by cultivating a newly isolated Streptomyces sp. ME98-M3 (FERM p-3722) in a medium containing a carbon source and a nitrogen source under aerobic conditions until a substancial amount of physiological activity has been produced and by recovering thus produced amastatins from the culture broth.

There are also provided by this invention various amastatin derivatives, such as salt, ester or N-acylated derivatives which are prepared by a conventional chemical process.

Amastatins and derivatives thereof have a powerful inhibitory effect on aminopeptidase A and enhance antibody formation. Therefore, the present invention also provides an inhibitory agent of aminopeptidase A containing amastatins and a composition for enhancing antibody formation.

DETAILED DESCRIPTION OF THE INVENTION

Amastatins $A_1$, $A_2$, $A_3$, $B_1$ and $B_2$ of the present invention are structurally related to each other. They have similar physicochemical properties as follows: melting points, elementary analyses, pKa, Rf values in thin layer chromatography and migrations in high voltage paper electrophoresis which are summarized in Table I.

TABLE I

Physicochemical properties of amastatins

| | Amastatins | | | | |
| --- | --- | --- | --- | --- | --- |
| | A1 | A2 | A3 | B1 | B2 |
| mp | 200–203 | 202–205 | 196–200 | 195–197 | 196–200 |
| Elementary analysis | | | | | |
| Found C | 53.06 | 53.00 | 54.30 | 54.00 | 54.31 |
| H | 8.32 | 7.91 | 8.01 | 8.40 | 7.98 |
| O | 14.61 | 27.17 | 11.16 | 23.02 | 11.21 |
| N | 23.30 | 11.67 | 26.10 | 14.18 | 26.00 |
| Calculated | | | | | |
| C | 53.26 | 53.15 | 54.08 | 54.19 | 54.08 |
| H | 8.30 | 8.07 | 8.25 | 8.48 | 8.25 |
| O | 14.79 | 11.81 | 11.47 | 22.97 | 11.47 |
| N | 23.65 | 26.98 | 26.20 | 14.36 | 26.20 |
| For | $C_{21}H_{39}N_5O_7$ | $C_{21}H_{38}N_4O_8$ | $C_{22}H_{40}N_4O_8$ | $C_{22}H_{41}N_5O_7$ | $C_{22}H_{40}N_4O_8$ |
| M.W. | 473 | 474 | 488 | 487 | 488 |
| pKa | 3.8 | 2.8 | 3.0 | 3.7 | 3.0 |
| | | 4.0 | 4.2 | | 4.2 |
| Rf value* | 0.47 | 0.46 | 0.54 | 0.55 | 0.52 |
| Rm value** | 0.52 | 0.51 | 0.53 | 0.54 | 0.53 |

*Thin layer chromatography was performed with a silica gel plate and a solvent system of n-butanol - acetic acid - water (4:1:1).
**Relative migration distance toward a cathode to alanine with a buffer solution of formic acid - acetic acid - water (25:75:900) at 3500v for 15min.

Amastatins $A_1$, $A_2$, $A_3$, $B_1$ and $B_2$ are soluble in water, methanol, acetic acid, pyridine and dimethyl sulfoxide, are slightly soluble in n-propanol and n-butanol and are almost insoluble in ethyl acetate, butyl acetate, diethyl ether, n-hexane, petroleum ether, benzene and chloroform. They give positive Rydon-Smith, ninhydrin and potassium permanganate reactions but negative Ehrlich and Sakaguchi reactions. No characteristic ultraviolet absorption is observed. Amastatins are stable in neutral, acidic and alkaline solutions. The inhibitory activity on aminopeptidase A was not decreased by heating the aqueous solution of pH 2, 7 or 9 at 60° C. for 30 min.

The following paragraphs describe the structures of amastatins which have thus far been characterized.

Amastatin A₁

In the infrared absorption spectrum in potassium bromide the following absorption peaks are observed: 3300, 2980, 1710, 1665, 1635, 1550, 1470, 1405, 1355, 1225, 1150, 1090 and 700 (cm⁻¹). Amino acid analysis of the acid hydrolysate of the compound in 6NHCl at 105° C. for 18 hours gives valine, aspartic acid and a previously unknown amino acid with a molar ratio of 2:1:1. The new amino acid is isolated and purified by resin chromatography; its structure was suggested by NMR spectrum, IR spectrum, elementary analysis, pKa value, color reactions and chemical reactions, and confirmed by the chemical synthesis to be as follows:

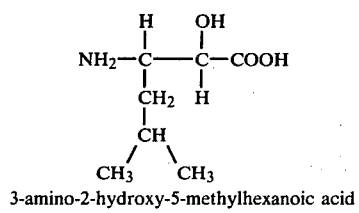

3-amino-2-hydroxy-5-methylhexanoic acid

The NMR spectrum (100 MHz. in D₂O) of amastatin A₁ shows signals at δ 1.1–1.4, 1.6–2.1, 2.2–2.6, 3.0–3.2, 3.85–3.95 and 4.4–4.7. For further characterization the peptide was acetylated at the N-terminal and dimethyl ester of N-acetylamastatin A₁ was subjected to mass analysis. The result revealed that these amino acids were bound by amide bonds in sequence of N-acetylated new amino acid, valine, valine and aspartic acid dimethyl ester from the N-terminal. The above-mentioned pKa value of 3.8 indicates that the β-carboxyl group of aspartic acid at the C-terminal of the peptide is free and the other α-carboxyl group forms an acid amide. The structure of amastatin A₁ has thus been determined as follows:

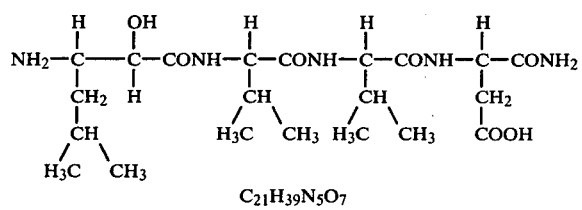

C₂₁H₃₉N₅O₇

3-amino-2-hydroxy-5-methylhexanoyl-L-valyl-L-valyl-L-aspartic acidα-amide

Amastatin A₂

The IR spectrum (KBr) gives the following peaks: 3400, 3250, 3030, 2930, 1700, 1650, 1620, 1530, 1465, 1390, 1220, 1160, 1085 and 700 (cm⁻¹). Amino acid analysis provides the same result as in amastatin A₁. The new amino acid has also been identified to be the same amino acid as that of amastatin A₁ by the above-mentioned procedures. In the NMR spectrum of amastatin A₂ the signals are observed at δ 1.2–1.5, 1.9–2.1, 2.3–2.7, 3.15–3.35, 3.85–4.15, 4.5–4.8 and 4.9–5.1. High-resolution mass spectrometric analysis of N-acetyl amastatin dimethyl ester demonstrates the same amino acid sequence as that of amastatin A₁. The elementary analysis and the pKa values of 2.8 and 4.0, however, indicate that the two carbonyl groups of aspartic acid are carboxylic acid. The determined structure is as follows:

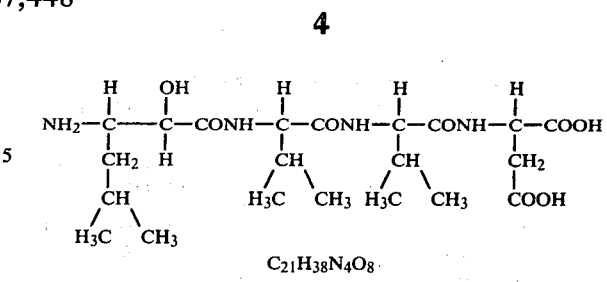

C₂₁H₃₈N₄O₈

3-amino-2-hydroxy-5-methylhexanoyl-L-valyl-L-valyl-L-aspartic acid

Amastatin A₃

The IR spectrum (KBr) of the compound has the following peaks: 3430, 3280, 2950, 1710, 1660, 1630, 1540, 1467, 1395, 1225, 1090, 960 and 700 (cm⁻¹). Amino acid analysis of the acid hydrolysate gives valine, glutamic acid and unknown amino acid. The new amino acid has been identified to be the same as in A₁ and A₂. The NMR spectrum of amastatin A₃ shows the signals at δ 1.2–1.6, 2.3–2.7, 2.7–3.0, 3.1–3.4, 3.8–4.4 and 4.4–4.9. The high-resolution mass spectrum of N-acetyl amastatin A₃ dimethyl ester indicates that N-acetylated new amino acid, valine, valine and glutamic acid dimethyl ester are bound in that order from the N-terminal to form amide bonds. The pKa values of 3.0 and 4.2 suggests that the α- and γ-carbonyl groups of glutamic acid are carboxylic acid. From these results, the structure of amastatin A₃ has been determined to be the following:

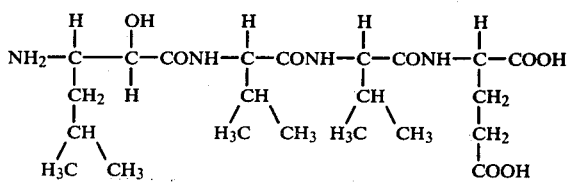

C₂₂H₄₀N₄O₈

3-amino-2-hydroxy-5-methylhexanoyl-L-valyl-L-glutamic acid

Amastatin B₁

In the IR spectrum the following absorption bands are exhibited: 3340, 3000, 1710, 1665, 1640, 1550, 1475, 1405, 1315, 1230, 1160, 1090, 960 and 700 (cm⁻¹). Amino acid analysis of the acid hydrolysate of the amastatin B₁ in 6NHCl at 105° C. for 18 hours gives valine, glutamic acid and unknown amino acid in the molar ratio of 2:1:1. The new amino acid has been isolated and purified, and characterized by NMR analysis. The structure of the amino acid has been found to be as follows by chemical synthesis.

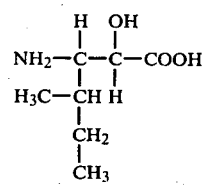

3-amino-2-hydroxy-4-methylhexoanoic acid

Amastatin B₁ gives NMR spectrum (100 MHz in D₂O) which shows the signals at δ 0.6–1.0, 1.2–1.55, 1.6–2.3, 2.95–3.3, 3.8–4.4, 7.4–7.7 and 7.9–8.3. Analysis of high-resolution mass spectrum of N-acetyl amastatin B₁ dimethyl ester indicates that N-acetylated new amino acid, valine, valine and glutamic acid dimethyl ester are bound by amide bonds in the sequence mentioned. It is suggested by the pKa value of 3.7 that the γ-carbonyl group of glutamic acid bound at the C-terminal side is carboxylic acid and the other α-carbonyl group is an acid amide. Thus, the structure of amastatin B₁ has been determined as follows:

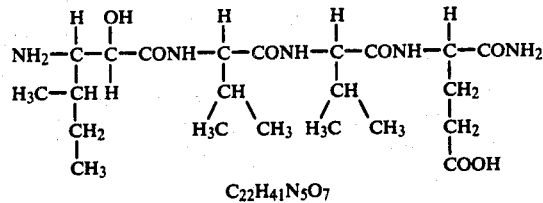

C₂₂H₄₁N₅O₇

3-amino-2-hydroxy-4-methylhexanoyl-L-valyl-L-valyl-L-glutamic acid α-amide

Amastatin B₂

In the IR spectrum the following absorption maxima are observed: 3400, 3260, 2940, 1700, 1655, 1625, 1550, 1450, 1400, 1315, 1225, 1150, 1090, 950 and 700 (cm⁻¹). The same three amino acids are detected as in amastatin B₁. The NMR spectrum (100 MHz in D₂O) shows the signals at δ 1.1–1.55, 2.1–2.35, 2.37–2.75, 2.8–3.2, 3.8–4.05, 4.45–4.7, 4.75–4.9 and 4.9–5.0. The assignment of high-resolution mass spectrum of N-acetylated amastatin B₂ dimethyl ester revealed that N-acetyl new amino acid, two valines and glutamic acid dimethyl ester are bound in that sequence by amide bonds. The pKa values of 3.0 and 4.2 indicate that the two carbonyl groups of glutamic acid are carboxylic acid. The structure of amastatin B₂ is as follows:

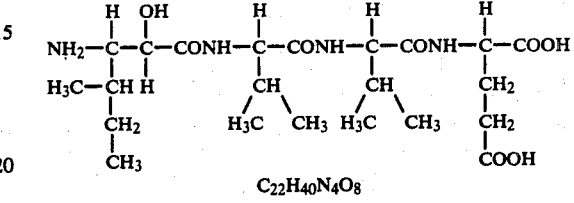

C₂₂H₄₀N₄O₈

3-amino-2-hydroxy-4-methylhexanoyl-L-valyl-L-valyl-L-glutamic acid

For further comfirmation of the structures of amastatins mentioned above, the novel peptides were chemically synthesized according to the following scheme:

Synthesis of the new amino acid of amastatin

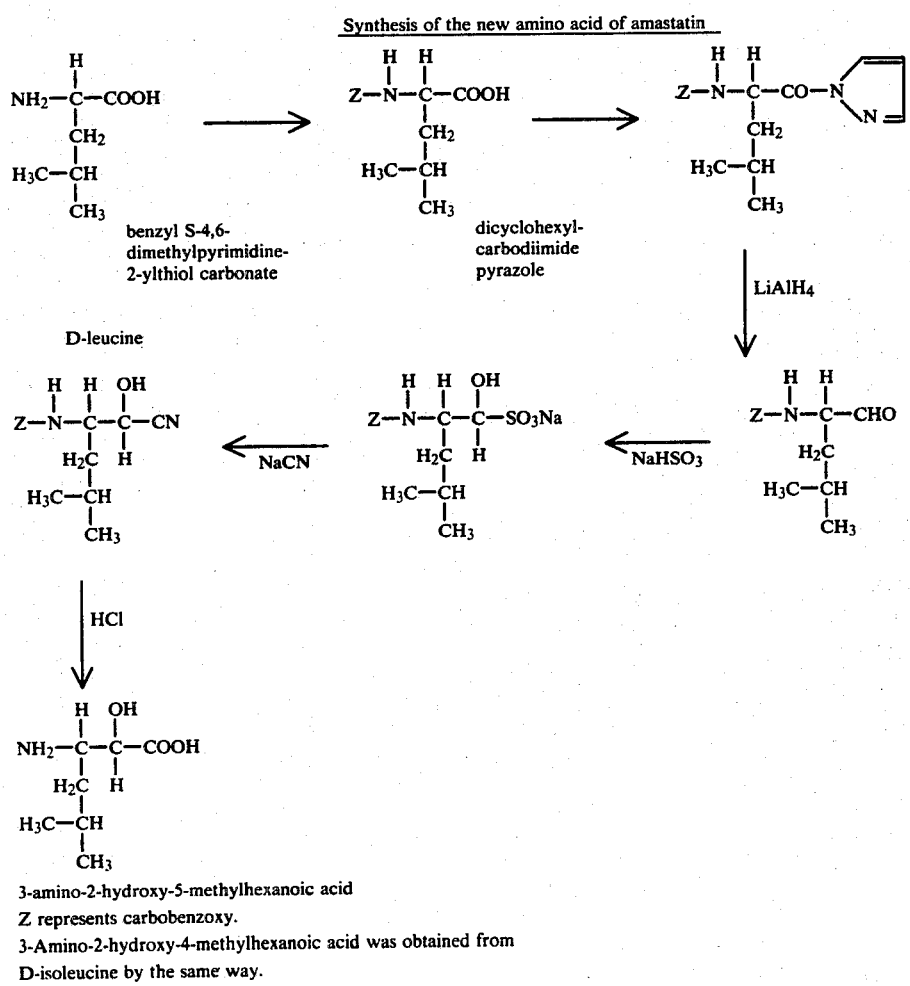

3-amino-2-hydroxy-5-methylhexanoic acid

Z represents carbobenzoxy.

3-Amino-2-hydroxy-4-methylhexanoic acid was obtained from D-isoleucine by the same way.

Chemical synthesis of amastatin

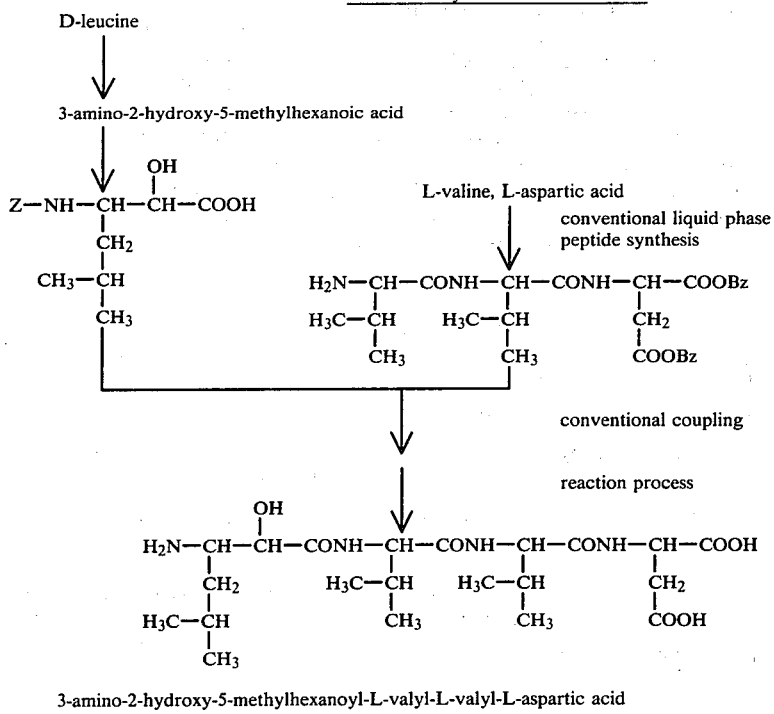

3-amino-2-hydroxy-5-methylhexanoyl-L-valyl-L-valyl-L-aspartic acid

Other analogues were synthesized according to the same scheme with isoleucine or glutamic acid.

The physicochemical properties of amastatins obtained by the process according to the present invention are in good agreement with those of the chemically synthesized peptides. Therefore, the aforementioned structures of amastatins have been supported and confirmed.

Amastatins contain one amino group and one carboxyl group in cases of $A_1$, $A_3$ and $B_1$ and one amino group and two carboxyl groups in cases of $A_2$ and $B_2$ which are capable of forming salts, esters and acylated derivatives by conventional methods. The present invention thus includes such amastatin derivatives.

Another aspect of this invention is to provide a process for preparation of the amastatins which comprises cultivating an amastatin-producing strain belonging to Genus Streptomyces in a suitable medium containing a carbon source and a nitrogen source under aerobic conditions until amastatins are substantially produced in the culture broth and recovering amastatins thus produced by conventional methods.

The microorganism useful for the preparation of amastatins has been taxonomically characterized as Streptomyces sp. ME98-M3. It was isolated from a soil as a strain ME98-M3 and depositted in the Fermentation Research Institute, Japan as FERM p-3722 and in the American Type Culture Collection, Rockville, Md, as A.T.C.C. 31318. The morphological and cultural characteristics of the strain are set forth in the following paragraphs.

1. Morphology

Aerial hyphae with curved or loop-shaped termenals extend from branched substrate hyphae. Mature space chain has 10 and more spores, which are $0.6$–$0.8 \times 1.0$–$1.2\mu$ with smooth surfaces.

2. Growth on various media

The description in parenthesis follows the color standard "Color Harmony Manual" published by Container Coporation of America, U.S.A.

(a) Sucrose-nitrate agar
   Vegitative growth: Dark yellow (3mc, Amber) No soluble pigment.
   Aerial mycelium: White (a, White) to pale yellowish brown (1½gc, Dusty Yellow)

(b) Glucose-asparagine agar
   Vegetative growth: Yellowish brown (3ne, Topaz Butterscotch). No soluble pigment.
   Aerial mycelium: Light gray (3fe, Silver gray).

(c) Glycerine-asparagine agar (ISP medium No 5)
   Vegetative growth: Yellowish brown (3ne, Topaz Butterscotch). No soluble pigment.
   Aerial mycelium: Light gray (3fe, Silver gray).

(d) Starch-inorganic salts agar (ISP medium No 4)
   Vegetative growth: Dark yellow (2ne, Mustard Gold) to pale yellow (2ne, Old Gold). No soluble pigment.
   Aerial mycelium: Yellowish gray (2ea, Lt. Wheat to Lt. Maze).

(e) Tyrosine agar (ISP medium No 7)
   Vegetative growth: Grayish yellow brown (3ni, Clove Brown). No soluble pigment.
   Aerial mycelium: Grayish white (b, Oyster White) to yellowish gray (2ca, Lt. Ivory).

(f) Nutrient agar
   Vegetative growth: Pale yellowish brown (3pe, Amber Topaz). No soluble pigment.
   Aerial mycelium: None.

(g) Yeast extract-malt extract agar (ISP medium No 2)
   Vegetative growth: Dark yellowish orange (3pg, Golden Brown). No soluble pigment.
   Aerial mycelium: White (a, White).

(h) Oatmeal agar (ISP medium No 3)
   Vegetative growth: Dark yellow (2nc, Brite Gold to Nugget Gold). No soluble pigment.

Aerial mycelium: Yellowish gray (2ca, Lt. Ivory).
(i) Peptone-yeast extract-iron agar (ISP medium No 6)
  Vegetative growth: Colorless to pale yellowish brown (2ga, Colonial Yellow, Maize). No soluble pigment.
  Aerial mycelium: None.
(j) Calcium malate agar
  Vegetable growth: Colorless to pale yellow (1½ia, Sunlight Yellow, Daffodil, Forsythia Jonquil). No soluble pigment.
  Aerial mycelium: White (a, White).

All of the observations mentioned above were carried out after incubation at 27° C.

3. Physiological properties
(a) Growth temperature: Optium temperature for growth is 24°–30° C. on maltose-yeast extract agar (maltose 10.0 g, yeast extract 4.0 g, agar 17.0 g and deionized water 1000 ml, pH 7.0). No growth below 15° C. and over 45 C.
(b) Gelatin Liquefaction on glucose-peptone-gelatin medium at 27° C.: Liquefaction begins after 5 days incubation and is completed at 21 days. Weak liquefaction.
(c) Starch hydrolysis on starch-inorganic salts agar (ISP medium No 4) at 27° C.: Very weak hydrolysis begins after about 5 days incubation.
(d) Peptonization and coagulation of skimmed milk at 37° C.: Coagulation is completed after 4 days incubation and then moderate peptonization begins.
(e) Melanin formation on tryptone-yeast extract broth (ISP medium No 1), peptone-yeast extract-iron agar (ISP medium No 6) and tyrosine agar (ISP medium No 7) at 27° C.: Negative on all the media.
(f) Utilization of carbohydrates of Pridham-Gottlieb agar at 27° C.: L-Arabinose, xylose, glucose, D-fructose, sucrose, inositol and raffinose: Good growth; L-rhamnose and cellulose: No growth.
(g) Liquefaction of calcium malate on calcium malate agar at 27° C.: Negative.

Based on the above-mentioned characteristics the strain ME 98-M 3 was identified as belonging to the genus Streptomyces and designated Streptomyces sp. ME 98-M 3.

Production of amastatins by a strain belonging to genus Streptomyces was discovered by this invention. The present invention thus includes all strains belonging to genus Streptomyces which produce the tetrapeptides according to this invention and the above-mentioned Streptomyces sp. ME98-M3 strain comprises all natural and artificial mutants and all strains which may belong to the same species as the embodiment of the microorganism according to the present invention.

Amastatins may be obtained by cultivation of the microorganism on a suitable medium and under suitable conditions. The media used for growth of the microorganisms in the present invention are the nutrient media known as suitable for growth of actinomycetes. As the carbon source any of those carbohydrates may be used which are normally employed in fermentation, such as glycerine, glucose, starch, dextrin, lactose, sucrose, maltose, molasses and fat may be also be employed. The nitrogen may be furnished by any of those materials which are usually used, such as peptone, meat extract, corn steep liquor, cottonseed metal, nuts meal, soybean meal, yeast extract, casamino acid, sodium nitrate, ammonium nitrate and ammonium sulfate. The media may contain sodium chloride, phosphate salts, calcium carbonate and magnesium sulfate as inorganic nutrients. Other metal salts may also be added as a trace element if required. The cultivation or fermentation may be conducted in any type of aerobic cultivation such as shaking-flask-culture or tank-fermentor-culture. Submerged culture is preferred for large scale production. The fermentation temperature should be selected in the range that the microorganism produces amastatins and, in particular, a range from 25° C. to 35° C. is preferable. The fermentation is generally continued until a substantial amount of amastatins has been produced in the cultured broth.

Amastatin production can be assayed by measuring the inhibitory activity on aminopeptidase A. The assay method employed is as follows: The aminopeptidase A activity was measured according to Nagatsu et al (I. Nagatsu, T. Nagatsu, T. Yamamoto and G. G. Glenner, Biochim. Biophys. Acta 198 255–70, 1970) with a modification. A mixture of 0.00075 M glutamyl-$\beta$-naphthylamide (1.0 ml), 0.01 M $CaCl_2$ (0.2 ml) 0.1 M tris-HCl buffer solution (pH 7.0, 0.6 ml) and a sample solution (0.1 ml) was incubated at 37° C. for 3 min. Aminopeptidase A solution (0.1 ml, prepared by ammonium sulfate fractionation according to Nagatsu's method) was added to the mixture. The incubation at 37° C. was continued for further 30 min. and then 1.0 M acetate buffer solution, pH 4.2 (0.6 ml) containing 0.1% fast garnet GBC salt (o-aminoazotoluene diazonium salt) and 10% Tween 20 was added. After 15 min. at room temperature absorbance (a) at 530 nm of the mixture was measured. A mixture without the sample was also treated in the same way as the control (b). An inhibition rate (%) of aminopeptidase A was calculated from the following equation:

$$\frac{b-a}{b} \times 100$$

The concentrations necessary for 50% of the inhibition rate ($ID_{50}$) in this assay tube were 0.65 mcg/ml in amastatin $A_1$, 0.54 mcg/ml in $A_2$, 1.0 mcg/ml in $A_3$, 1.5 mcg/ml in $B_1$ and 1.0 mcg/ml in $B_2$, respectively.

For example, a medium containing 2% glycerine, 2% dextrose, 1% Bactosoyton (Difco), 0.3% yeast extract, 0.2% $(NH_4)_2SO_4$ and 0.2% $CaCO_3$, pH 7.4, was autoclaved and inoculated with spores and/or mycelium obtained from a slant culture of Streptomyces sp. ME98-M3. All the expressions "%" means weight per volum in this specification unless noted otherwise. Amastatins accumulation was detected after 3–7 days aerobic shaking culture at 27° C.

Table 2 shows the production of amastatins in shaking cultures with various media. The fermentation was carried out using 100 ml of the medium in a 500 ml -flask on a rotary shaker (180 RPM) at 29° C. and 0.5 ml of the broth was sampled for the assay.

TABLE 2

Amastatin production in various culture media

| No. | Composition of medium | | Initial pH | \multicolumn{5}{c|}{Amastatin production Inhibition (%) Day} | Final pH |
|---|---|---|---|---|---|---|---|---|---|
| | | | | 1 | 2 | 3 | 4 | 7 | |
| 1. | Starch | 1.0 | 6.7 | | | | | 31.5 | 8.6 |
| | Glucose | 1.0 | | | | | | | |
| | Soy bean meal | 2.0 | | | | | | | |
| | Yeast extract | 0.5 | | | | | | | |
| 2. | Soy bean oil | 2.0 | 7.1 | | | | | 26.9 | 9.0 |
| | Starch | 0.5 | | | | | | | |
| | Glucose | 0.5 | | | | | | | |
| | Soy bean meal | 2.5 | | | | | | | |
| 3. | Glycerine | 2.5 | 7.0 | | | | | 23.2 | 9.1 |
| | Meat extract | 0.5 | | | | | | | |
| | Polypeptone | 0.5 | | | | | | | |
| 4. | Maltose | 2.0 | 7.8 | | | | | 17.6 | 9.3 |
| | Meat extract | 0.5 | | | | | | | |
| | Polypeptone | 0.5 | | | | | | | |
| | Yeast extract | 0.3 | | | | | | | |
| 5. | Starch | 2.0 | 7.1 | 26.2 | 31.6 | 35.3 | 33.5 | 46.2 | 8.1 |
| | Glucose | 1.0 | | | | | | | |
| | Yeast extract | 0.5 | | | | | | | |
| | Casamino acid | 0.5 | | | | | | | |
| 6. | Lactose | 2.5 | 7.8 | | | | | 26.0 | 9.4 |
| | Yeast extract | 0.5 | | | | | | | |
| | Meat extract | 0.5 | | | | | | | |
| | Polypeptone | 0.75 | | | | | | | |
| 7. | Sucrose | 4.0 | 7.9 | | | | | 22.2 | 9.5 |
| | Protein hydrolysate | 2.5 | | | | | | | |
| 8. | Glycerine | 2.0 | 6.9 | 40.0 | 52.7 | 52.7 | 50.2 | 49.1 | 8.2 |
| | Dextrine | 2.0 | | | | | | | |
| | Soypeptone* | 1.0 | | | | | | | |
| | Yeast extract | 0.3 | | | | | | | |
| 9. | Starch | 2.0 | 7.1 | 38.5 | 45.7 | 47.5 | 40.3 | 48.3 | 8.9 |
| | Cotton seed meal | 2.0 | | | | | | | |
| | Corn steep liquor | 1.0 | | | | | | | |
| 10. | Glycerine | 3.0 | 7.2 | | | | | 19.5 | 8.6 |
| | Fish meal | 2.0 | | | | | | | |

*Soypeptone is an enzymatic digest of soy bean meal

Table 3 also shows the amastatin production in various media. The carbon and the nitrogen sources shown in the table were added to a basal medium containing 0.1% yeast extract, 0.1% NaCl, 0.05% $K_2HPO_4$ and 0.05% $MgSO_4.7H_2O$. The fermentation was conducted with 50 ml medium in a 500 ml flask on a rotary shaker (200 RPM) at 28° C. the inhibitory activity was assayed with 0.02 ml of the broth.

TABLE 3

Amastatin production in various media

| No. | Composition of medium (%) Carbon source | | Nitrogen source | | pH | Amastatin production after 4 days incubation Inhibition (%) |
|---|---|---|---|---|---|---|
| A | Starch | 3.0 | Soy bean meal | 2.0 | 6.7 | 18.0 |
| B | | | Dry yeast | 3.0 | 6.1 | 23.0 |
| C | | 6.0 | | 4.0 | 6.8 | 41.3 |
| D | | | Cotton seed meal | 3.0 | 2.0 | 6.5 | 25.9 |
| E | | 6.0 | | 4.0 | 6.5 | 58.6 |
| F | Glycerine | 3.0 | Soy bean meal | 2.0 | 8.4 | 15.2 |
| G | | 3.0 | Dry yeast | 2.0 | 8.2 | 16.0 |
| H | | | Cotton seed meal | 3.0 | 2.0 | 8.3 | 17.1 |
| I | Soy bean oil | 3.0 | Soy bean meal | 2.0 | 7.4 | 43.1 |
| J | | 6.0 | | 4.0 | 6.8 | 55.1 |
| K | | 3.0 | Dry yeast | 2.0 | 7.4 | 36.6 |
| L | | 6.0 | | 4.0 | 6.9 | 46.1 |
| M | | | Cotton seed meal | 3.0 | 2.0 | 6.4 | 30.4 |
| N | Starch Soy bean meal | 4.5 1.5 | Dry yeast | 4.0 | 6.4 | 57.1 |
| O | | | Cotton seed meal | 4.0 | 6.5 | 61.8 |
| P | Starch | 6.0 | Cotton seed meal | 4.0 | 6.0 | 64.3 |

TABLE 3-continued

| | Amastatin production in various media | | | |
|---|---|---|---|---|
| | Composition of medium (%) | | Amastatin production after 4 days incubation | |
| No. | Carbon source | Nitrogen source | pH | Inhibition (%) |
| | | $(NH_4)_2SO_4$ | 0.2 | |

Soy bean meal: "Es-san meat", Ajinomoto Co.
Cotton seed meal: "Pharmamedia"

These results show the the amastatin production varies with medium and incubation time. Preferable ingredients of the medium for amastatin production are glycerine, glucose, starch, soy bean oil, soy peptone, cotton sead meal, corn steep liquor, soy bean meal, yeast, casamino acid and ammonium sulfate.

Jar and tank fermentors also give a good production of amastatin. For example, a tank-scale submerged culture was performed with 100 l of the medium P of Tab.3 in a 200 l fermentor. After 96 hours incubation with 100 l/min. aeration and 200 RPM agitation, the highest production of amastatin was obtained and 0.1 ml of the broth at the time gave 50% inhibition in the above-mentioned assay method. Amastatin analogues, i.e., $A_1$, $A_2$, $A_3$, $B_1$ and $B_2$ are usually coproduced in the fermentation broth. The ratio of each analogue in the broth depends on strain of microoganism, medium, cultural conditions and the like.

Amastatins thus produced in the fermentation broth may be recovered by any method which may be employed for isolation and purification of peptide and conventional per se. For a small scale isolation the broth filtrate is evaporated in vacuo to dryness and the residue is extracted with a solvent that can dissolve peptide, such as methanol, ethanol, dimethyl sulfoxide, acetic acid or pyridine. For a large scale work amastatins are extracted from the broth filtrate with a solvent that can dissolve peptide and is immiscible with water, such as n-butanol. Concentration of the extracts gives crude power of amastatins.

Amastatins are satisfactorily isolated by adsorption on a conventional adsorvant, e.g. active carbon, organic adsorvant such as Amberlite XAD-4 (Rohm and Haas Co.) and cellulose, ion exchangers and silica gel. For example, active carbon was added in the broth filtrate (2% to adsorb the peptides. The active carbon was filtered off and washed with water and then with 20-25 volumes of methanol at 40° C. twice. More than 70% of amastatin in the broth was obtained by the methanol elution. Coproduced amastatin analogues are thus isolated as a crude powder of their mixture. Each amastatin analogue may effectively be fractionated and purified by chromatography. For this purpose cellulose is employed with a mixture of ethyl acetate-ethanol-ammonia (17:2:1) as a preferable solvent system. Isolation and purification are also possible by means of ion exchange resin based on the acidic and the basic functional groups of amastatins. Strongly basic or strongly acidic ion exchange resin is preferred.

The present invention also includes a process for preparation of amastatin derivatives. Metal salts of amastatins are easily obtained by neutralization. Another salt form of amastatin is prepared by crystalization after addition of inorganic acid such as hydrochloric acid since amastatins have a free amino group. N-Acylated derivatives are obtained by the treatment with anhydride or halide of organic acid, such as acetic acid and propionic acid, under suitable conditions. Amastatins $A_2$, $A_3$ and $B_2$ (22 mg, 20 mg and 20 mg, respectively) were dissolved in water. Acetyl chloride was added to the solution at pH 8.5 to acetylate the free amino group. N-Acetyl amastatins $A_2$, $A_3$ $_{1\ and\ B_2}$ were obtained with the yields of 13 mg, 11 mg and 10 mg, respectively. The NMR and the IR spectra confirmed that the products were N-acetylated amastatins. Esters of amastatins are prepared by esterification of the free carboxyl group with alcohol under suitable conditions. To N-acetyl amastatins $A_2$, $A_3$ and $B_2$ (9 mg, 8 mg and 8 mg, respectively) was added a mixture of thionyl chloride (0.5 ml) and methanol (4 ml) in an ice bath. The reaction mixture was kept in the ice for 30 min. and then at room temperature overnight. Evaporation in vauco to dryness gave N-acetyl amastatin dimethyl ester (10 mg of $A_2$, 9 mg of $A_3$ and 9 mg of $B_2$ dimethyl esters, respectively). The NMR and the mass spectra confirmed that the products were dimethyl esters of N-acetyl amastatins $A_2$, $A_3$ and $B_2$, respectively. Therefore, the present invention comprises processes for preparations of salts, N-acylated derivatives and esters of amastatins.

Amastatins of this invention possess a powerful inhibitory activity on aminopeptidase A as aformentioned. The inhibitory activity is so specific to aminopeptidase A that other aminopeptidases, such as aminopeptidases B are insusceptible to the tetrapeptides. Table 4 shows $ID_{50}$ values of amastatins with aminopeptidase A and B.

TABLE 4

| Inhibitions of aminopeptidase A and B by amastatins | | |
|---|---|---|
| | $ID_{50}$ (mcg/ml) | |
| Amastatins | Aminopeptidase A | Aminopeptidase B |
| $A_1$ | 0.65 | >100 |
| $A_2$ | 0.54 | >100 |
| $A_3$ | 1.0 | >100 |
| $B_1$ | 1.5 | >100 |
| $B_2$ | 1.0 | >100 |

Aminopeptidase A is inhibited at the concentration of 0.5-1.5 mcg/ml but aminopeptidase b is not affected even in the presence of 100 mcg/ml amastatin.

In addition to the inhibitory activity, the novel tetrapeptides of this invention show stimulation of humoral antibody formation. When mice (dd/Y) were immunized by intravenous injection of $10^8$ sheep red blood cells (SRBC), amastatins in saline were administered intraperitoneally or orally to the mice. Four days thereafter, the number of plaque forming cell (PFC) in spleen were enumerated by Jerne'S homolytic plaque technique (N. K. Jerne., A. A. Nordin and C. Henry: The agar plaque technique for recognizing antibody-producing cells, Cell-bond Antibodies. B. Amos and H. Koprowskied. pp. 109–122, Wister Institute Press, Philadelphia, 1963; N. K. Jerne and A. A. Nordine, Plaque Formation in Agar by Single Antibody-Producing Cells, Science, 140, pp 405, 1963).

As shown in Table 5, the intraperitoneal injection of 1 to 1000 mcg/mouse or the oral administration of 10 to 1000 mcg/mouse of amastatin $A_2$ led to increase the number of plaque-forming cells (PFC) about two or three times compared to the number of PFC in antigen alone.

Table 5.

Effect of Amastatin on Antibody Formation to SRBC (I) in Mice

| | Amastatin $A_2$ dose/mouse* | Amst. administrated by i.p. PFC/spleen | oral |
|---|---|---|---|
| $10^8$ SRBC | 0 | 149,000 | 125,000 |
| " | 1,000 μg | 235,000 | 153,000 |
| " | 100 | 283,000 | 192,800 |
| " | 10 | 504,000 | 286,400 |
| " | 1 | 264,800 | 102,700 |

*injected i.p. at a time of immunization

After amastatin $A_2$ was injected intraperitoneal once a day to mice for four days, mice were immunized by intravenous injection of $10^8$ SRBC. Four days after the immunization, the number of antibody-forming cells in spleen of mice were enumerated. As the result, intraperitoneal injection of 100 to 1000 mcg/mouse/day of amastatin $A_2$ increased the number of PFC about two or three times compared to the number of PFC in antigen alone.

Table 6.

Effect of Amastatin on Antibody Formation to SRBC (II) in Mice

| dose in μg/mouse* | SRBC** | PFC/spleen |
|---|---|---|
| 0 | $10^8$ SRBC | 76,000 |
| 1,000 | " | 121,000 |
| 100 | " | 138,000 |
| 10 | " | 196,000 |
| 1 | " | 58,000 |

*days −4 ∼ −1, i.p.
**day 0, i.v.

The effect of amastatin on primary antibody formation against SRBC in dissociated spleen cell cultures was examined according to the methods described by Mishell and Dutton. Spleen all cultures (1.5 × $10^7$) were prepared from spleens of $CDF_1$ mice and were cultured with $10^6$ SRBC as antigen for 4 days at 37° C. in 7% $CO_2$ atmosphere. Amastatin was dissolved in medium and each concentration of amastatin in range of 0.0001 μg to 1 μg per culture was added at the time of the immunization (0 hour), 24, 48 or 72 hours after start of cultures. Four days after start of cultures, antibody formation of each culture was determined by enumerization in terms of PFC using the method described in Cuningham et al.

As shown in Table 7, addition of 0.01 to 1 μg of amastatin $A_2$ to spleen cell culture 0 or 24 hours after the start of cultures increased the number of PFC.

Table 7.

| Amastatin μg/culture | Additional of Amst. hrs. after start of culture | | | |
|---|---|---|---|---|
| | 0 | 24 | 48 | 72 |
| $10^6$ SRBC 0 | 2920 | — | — | — |
| " 1 | 4420 | 3100 | 2280 | 2520 |
| " 0.01 | 4200 | 2960 | 2380 | 3160 |
| " 0.0001 | 2900 | 3080 | 2940 | 3080 |

Also amastatin augmented establishment of delayed-type hypersensitivity (DTH) to SRBC. Female dd/Y mice were immunized by injection of $10^8$ SRBC in 0.05 ml of saline into the right hind footpad. Four days thereafter, the reaction was elicited by injection of $10^8$ SRBC into left hind footpad and the increase of the thickness of the left hind footpad was measured 24 hours later.

Amastatin $A_2$ was injected intraperitoneally once a day to the mice for four days before the immunization by $10^8$ SRBC. As shown in Table 8, amastatin $A_2$ of 0.1 to 10 mcg/mouse/day enhanced the footpad response, but the injection of 100 mcg/mouse/day did not show any effect on the footpad response. Also intraperitoneal injection of 1 to 1000 mcg/mouse of amastatin $A_2$ at the time of immunization did not enhance the footpad response.

Table 8.

Influence of Amastatin on Establishment of Delayed-Type Hypersensitivity to SRBC in Mice

| | Amst. injected on days or day | |
|---|---|---|
| dose in μg/mouse | −4 ∼ −1 Increase of Footpad thickness | 0* |
| 0 | 10.2 | 9.0 |
| 1,000 | — | 8.1 |
| 100 | 10.0 | 7.8 |
| 10 | 14.3 | 8.1 |
| 1 | 14.1 | 8.4 |
| 0.1 | 13.8 | — |

*at a time of immunization

The fact that amastatins enhance the antibody formation and the establishment of DTH shows possible application of the peptides to potentiate the host-defense system against bacterial and viral infections and also against cancer. Aminopeptidase A is one of the angiotensinases. Strong inhibition of the enzyme activity causes an inhibition of angiotensin II decomposition to maintain a certain concentration of angiotensin and to raise the blood pressure. Amastatins are possibly utilized for this purpose and also for potentiation of aldosterone activity.

Amastatins of this invention show very low toxicity. Conventional aminopeptidase A inhibitors are highly toxic substances, e.g. metal chelating agents such as ethylenediamine tetracetic acid or o-phenanthroline or protein-modifying agents. Amastatins show the inhibition at lower concentration and have much lower toxicity than the conventional inhibitors. Table 9 gives the acute toxicity of amastatins in mouse by the intraperitoneal administration.

TABLE 9

| | Toxicity of amastatins | |
|---|---|---|
| Amastatins | Dose (mg/kg, ip) | Toxicity |
| $A_1$ | 125 | none |
| $A_2$ | 125 | none |
| $A_3$ | 125 | none |
| $B_1$ | 125 | none |
| $B_2$ | 125 | none |

The following examples illustrate the present invention, but it is to be understood that they are given for the purpose of illustration and not limitation.

EXAMPLE 1

A medium (100 l) containing 6.0% soluble starch, 4.0% cotton seed meal, 0.2% $(NH_4)_2SO_4$, 0.1% yeast extract, 0.2% $CaCO_3$, 0.05% $K_2HPO_4$, 0.05% $MgSO_4.7H_2O$, 0.1% NaCl and 0.01% Adecanol (antifoam, Asahidenka Co.) was sterilized in a 200 l stainless steel fermentor at 120° C. for 30 min. and inoculated with a seed culture (5 l) of Streptomyces sp. ME98-M3 (FERM p- 3722) prepared with the same medium by flask culture. Submerged culture was performed at 27°

C. for 96 hours with 200 l/min. aeration and 200 RPM agitation. Filtered broth (200 l) was obtained from two batches of the fermentation.

The filtrate, of which $ID_{50}$ was 0.1 ml, was applied to a 3 l-column of Amberlite XAD(-4) (Rohm and Haas Co.). Amastatins were eluted with 30 l of 50% methanol. Concentration in vacuo of the eluate at 60° C. gave a crude powder of amastatins (390 g). The $ID_{50}$ value of the powder was 250 mcg/ml.

The powder (390 g) was dissolved in 3.9 l of water adjusting the pH to 8.2 with 1 N NaOH and the solution was applied to a Dowex 1 (×4) column (acetate type, 3.5 l, Dow Chemicals Co.). Elution with 10 l of 0.1 N acetic acid, after washing with 10 l of water, provided 110 g of active powder ($ID_{50}$=100 mcg/ml). This powder was dissolved in 1.1 l of 0.3 M pyridine-acetic acid buffer solution (pH 6.0) and applied to a DEAE-Sephadex A25 column (600 ml, Pharmacia Co.) previously equilibrated with the same buffer. An active peak obtained by the elution with the same buffer was concentrated in vacuo to give 30.6 g of active powder ($ID_{50}$=40 mcg/ml).

A solution of the active powder in 400 ml of 0.05 M pyridine-formic acid buffer solution (pH 2.9) was applied to a Dowex 50 (×4) column (310 ml, Dow Chemical Co.) previously equilibrated with the same buffer. An active peak was obtained by the elution with a linear gradient from 0.05 M, pH 2.9 to 0.2 M, pH 3.1 pyridine-formic acid buffer (2 l). Concentration in vacuo of the peak gave 5.1 g of active powder ($ID_{50}$=8.5 mcg/ml).

The powder was further purified by silica gel chromatography with a solvent system of n-butyl acetate-n-butanol-acetic acid-water (12:4:1:1). Highly active powder (0.8 g) was obtained ($ID_{50}$=2.5 mcg/ml). For fractionation of the active powder to each amastatin analogue, the above-mentioned Dowex 50 column chromatography was performed again. Amastatins $A_2$, $A_3$ and $B_2$ were separated each other by the rechromatography. Each powder obtained by concentration of the active fraction was desalted by adsorption on Dowex 50 (×4) ($H^+$ type) and by elution with 0.2 N $NH_4OH$. The following substantially pure amastatins were obtained:

$A_2$: 30 mg ($ID_{50}$ 0.54 mcg/ml),
$A_3$: 47 mg ($ID_{50}$ 1.0 mcg/ml) and
$B_2$: 20 mg ($ID_{50}$ 1.0 mcg/ml).

These preparations had the aforementioned physicochemical propertes.

EXAMPLE 2

A medium (125 ml) containing 2% potato starch, 2% cottonseed meal, 1% corn steep liquor and 0.32% $CaCO_3$ was sterilized in a 500 ml flask at 120° C. for 20 min., inoculated with Streptomyces sp. ME98-M3 (FERM p- 3722) and incubated at 27° C. with a reciprocal shaking at 130 RMP for 2 days. This culture was used as a seed.

A medium (15 l) containing 2% glycerine, 2% dextrin, 1% Bactosoytone (Difco Co.), 0.3% yeast extract, 0.2% $(NH_4)_2SO_4$ and 0.2% $CaCO_3$ was sterilized in a 30 l jar fermentor, inoculated with the seed culture (1 l) prepared as mentioned above and incubated with 15 l/min. aeration and 200 RPM agitation at 27° C. for 4 days. A broth filtrate (50 l), of which $ID_{50}$ was 0.14 ml, was obtained from 4 batches of the jar culture.

The filtrate was subjected to purification by the substancially same procedure as described in Example 1. The rechromatography of the active powder obtained by the silica gel treatment and the desalting by Dowex 50 gave 25 mg of substancially pure amastatin $A_1$ ($ID_{50}$=0.65 mcg/ml) and 35 mg of substancially pure amastatin $B_1$ ($ID_{50}$=1.50 mcg/ml). The physicochemical properties of the preparations were in good agreement with the aforementioneds.

EXAMPLE 3

Amastatins $A_1$ (3 mg) was dissolved in 0.5 ml of 0.1 N HCl and stood at room temperature for 1 hour. Concentration in vacuo of the solution and evaporation of excess hydrochloric acid provided hydrochloric acid salt of amastatin $A_1$. Salts of other analogues were obtained by the same method. These salts have the following properties:

HCL $A_1$: mp 165°–170° C.
  IR spectrum—3400, 3270, 2950, 1710, 1660, 1640, 1540, 1470, 1390, 1285, 1230, 1180, 1090 ($cm^{-1}$)
  $ID_{50}$—0.75 mcg/ml
$A_2$: mp 158°–162° C.
  IR spectrum—3300, 2950, 2600, 1725, 1660, 1640, 1535, 1470, 1395, 1280, 1230, 1180, 1090, 930 ($cm^{-1}$)
  $ID_{50}$—0.6 mcg/ml
$A_3$: mp 148°–153° C.
  IR spectrum—3250, 2930, 2600, 1710, 1650, 1635, 1530, 1465, 1390, 1220, 1113, 930 ($cm^{-1}$)
  $ID_{50}$—1.1 mcg/ml
$B_1$: mp 160°–165° C.
  IR spectrum—3400, 3270, 2950, 1710, 1655, 1635, 1540, 1470, 1390, 1290, 1230, 1170, 1070 ($cm^{-1}$)
  $ID_{50}$—1.8 mcg/ml
HCl.$B_2$: mp 145°–150° C.
  IR spectrum—3400, 3250, 2900, 1720, 1690, 1625, 1535, 1435, 1385, 1275, 1220, 1175, 1155, 1105, 1085, 1010, 985, 925, 790 ($cm^{-1}$)
  $ID_{50}$ 1.1 mcg/ml

EXAMPLE 4

Amastatin $A_2$ (22 mg) was dissolved in 10 ml of water. Acetyl chloride (0.5 ml) was added 4 times at 10 min. intervals stirring at room temperature and maintaining the pH at 8.5 with 1 N NaOH. After 2 hours, the pH was adjusted to 2.0 with conc. HCl and the mixture was extracted with 20 ml of ethyl acetate twice. Concentration in vacuo of the solvent layer gave 13 mg of the product.
  mp: 160°–164° C.,
  $ID_{50}$: 450 mcg/ml The IR and the NMR spectrum supported and confirmed that the product was N-acetyl amastatin $A_2$.

N-Acetyl amastatins $A_1$, $A_3$, $B_1$ and $B_2$ were obtained by the same method.

EXAMPLE 5

Amastatin $A_2$ (30 mg) was dissolved in 2 ml of absolute methanol. A mixture of thionyl chloride (1 ml) and absolute methanol (2 ml) was added with ice-cooling and the mixture was stirred with the cooling for 30 min. and then at room temperature overnight. Concentration in vacuo of the mixture gave 31 mg of the reaction product.
  mp: 148°–153° C.
  $ID_{50}$: 17 mcg/ml The IR and the NMR spectrum supported and confirmed that the product was amastatin $A_2$ dimethyl ester.

Dimethyl esters of amastatins A$_3$ and B$_2$ were obtained by the same method. N-Acetyl amastatins A$_2$, A$_3$ and B$_2$ gave dimethyl ester of each analog, respectively by the same way.

Monomethyl esters of amastatins A$_1$ and B$_1$ were also obtained by the same process.

The solid resin Amberlite XAD is a macroreticular, crosslinked polystyrene polymer (U.S. Pat. No. 3,531,463). Such macroporous nonionic adsorption resins have an aromatic basic structure with an average pore diameter of 4-20 nm, preferably 7-10 nm, especially polystyrene resins having a surface from 100 to 1,000 m$^2$ per gram which are styrene-divinylbenzene copolymers marketed by Rohm & Haas Co. as Amberlite XAD resins.

Dowex 50 is a polystyrene nuclear sulfonic acid.

"Sephadex LH-20" is a lyophilic insoluble molecular-sieve chromatographic medium made by cross-linking dextran and marketed by Pharmacia, Uppsala, Sweden.

Sephedex LH-20 can be replaced by other similar gel-filtration agents, e.g. Sephadex G25 to G200, Sepharose 4B and 6B (Pharmacia Fine Chemicals AB, Uppsala, Sweden) and Bio-Gel A1.5 m (Bio Rad Co.). Preferred gel-filtration agents include the carboxymethyl substituted cross-linked dextran gels described in columns 3 and 4 of U.S. Pat. No. 3,819,836.

Dowex 1-X2(OH$^-$) is the basic or hydroxide form of cholestyramine resin which in its chloride form is a synthetic, strongly basic anion exchange resin containing quaternary ammonium functional groups which are attached to a styrene-divinylbenzene copolymer. Main constituent: Polystyrene trimethylbenzylammonium as Cl$^-$ anion, also contains divinylbenzene (about 2%) and water

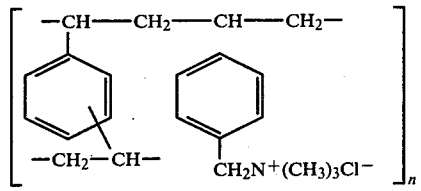

typified structure of main polymeric groups (about 43%). Cross linkage %: 1-10. Particle size: 50-100 mesh. Percent volume increase, new to exhausted (Cl$^-$ to OH$^-$)=20%. Stable at temperatures up to 150°. Capacity: 3.5 meq/g dry, 1.33 meq/ml wet.

We claim:

1. A process for producing a tetrapeptide of the formula $$X—Val—Val—Y \qquad I$$

wherein,
X represents 3-amino-2-hydroxy-5-methylhexanoyl residue or 3-amino-2-hydroxy-4-methylhexanoyl residue, Val represents L-valyl residue, and Y represents L-aspartic acid α-amide, L-aspartic acid or L-glutamic acid when X is 3-amino-2-hydroxy-5-methylhexanoyl residue and L-glutamic acid α-amide or L-glutamic acid when X is 3-amino-2-hydroxy-4-methylhexanoyl residue, and the amino group of the Val adjacent to X being acylated with the carboxyl group of the X to form an amide bond, the carboxyl group of said Val acylating the amino group of the other Val to form an amide bond and the carboxyl group of the other Val acylating the amino group of the Y to form an amide bond which comprises cultivating aerobically a microorganism that is capable of producing said tetrapeptide and belongs to the genus Streptomyces in a medium suitable for growth of said microorganism to accumulate said tetrapeptide and recovering said tetrapeptide thus produced.

2. A process for producing a tetrapeptide of the formula $$X—Val—Val—Y \qquad I$$

wherein,
X represents 3-amino-2-hydroxy-5-methylhexanoyl residue or 3-amino-2-hydroxy-4-methylhexanoyl residue, Val represents L-valyl residue, and Y represents L-aspartic acid α-amide, L-aspartic acid or L-glutamic acid when X is 3-amino-2-hydroxy-5-methylhexanoyl residue and L-glutamic acid α-amide or L-glutamic acid when X is 3-amino-2-hydroxy-4-methylhexanoyl residue, and the amino group of the Val adjacent to X being acylated with the carboxyl group of the X to form an amide bond, the carboxyl group of said Val acylating the amino group of the other Val to form an amide bond and the carboxyl group of the other Val acylating the amino group of the Y to form an amide bond which comprises cultivating aerobically a microorganism that is capable of producing said tetrapeptide, belongs to the genus Streptomyces and has the identifying characteristics of A.T.C.C. 31318 in a medium suitable for growth of said microorganism to accumulate said tetrapeptide and recovering said tetrapeptide thus produced.

* * * * *